United States Patent
Harm et al.

(10) Patent No.: US 11,530,965 B2
(45) Date of Patent: Dec. 20, 2022

(54) MONITORING DEVICE FOR A SYSTEM FOR GENERATING MEDICAL COMPRESSED AIR

(71) Applicant: Drägerwerk AG & Co. KGaA, Lübeck (DE)

(72) Inventors: Reiner Harm, Scharbeutz (DE); Kjer Martensen, Lübeck (DE); Matthias Losch, Lübeck (DE); Ronny Barten, Lübeck (DE); Stefan Reincke, Hamburg (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 496 days.

(21) Appl. No.: 16/616,038

(22) PCT Filed: May 23, 2018

(86) PCT No.: PCT/EP2018/063438
§ 371 (c)(1),
(2) Date: Nov. 22, 2019

(87) PCT Pub. No.: WO2018/215505
PCT Pub. Date: Nov. 29, 2018

(65) Prior Publication Data
US 2020/0088611 A1 Mar. 19, 2020

(30) Foreign Application Priority Data
May 24, 2017 (DE) .................... 10 2017 005 011.2

(51) Int. Cl.
*G01N 1/22* (2006.01)
*A61M 16/00* (2006.01)
(Continued)

(52) U.S. Cl.
CPC ....... *G01N 1/2247* (2013.01); *A61M 16/0051* (2013.01); *A61M 16/0063* (2014.02);
(Continued)

(58) Field of Classification Search
CPC .............. A61M 16/00; A61M 16/0051; A61M 16/0057; A61M 16/0063; A61M 16/0087;
(Continued)

(56) References Cited

U.S. PATENT DOCUMENTS 4,459,266 A * 7/1984 Lamoreaux .......... G01N 31/223
128/204.22
6,220,076 B1 4/2001 Layzell et al.
(Continued)

FOREIGN PATENT DOCUMENTS

DE 4312837 C1 10/1994
DE 10164667 C1 3/2003
(Continued)

OTHER PUBLICATIONS

Norm DIN EN ISO 7396-1 2016-09-00 Rohrleitungssysteme für medizinische Gase—Teil 1: Rohrleitungssysteme für medizinische Druckgase und Vakuum (ISO 7396-1 :2016); Deutsche Fassung EN ISO 7396-1 :2016. S. 1-206.

*Primary Examiner* — Joseph D. Boecker
(74) *Attorney, Agent, or Firm* — McGlew and Tuttle, P.C.

(57) ABSTRACT

A monitoring device (1) for a system for generating medical compressed air includes a measured air line (3) removing compressed air from a compressed air supply line downstream of a compressed air conditioning unit. A sensor (2) generates a measured signal as a function of a property of the compressed air fed through the measured air line. A humidifier (8) humidifies the compressed air upstream of the sensor. An output unit (12) outputs information about the property of the compressed air to a user on the basis of the measured
(Continued)

signal. A tap (4) removes compressed air and an actuator (5) changes a volume flow and/or mass flow of the compressed air, which volume flow and/or mass flow prevails in the measured air line. The actuator is inserted into the tap in a measuring mode and is removed from the tap in a compressed air removal mode.

20 Claims, 2 Drawing Sheets

(51) Int. Cl.
 *A61M 16/16* (2006.01)
 *G01N 33/00* (2006.01)
(52) U.S. Cl.
 CPC ........... *A61M 16/16* (2013.01); *G01N 33/004* (2013.01); *G01N 33/0018* (2013.01); *G01N 33/0063* (2013.01); *A61M 16/00* (2013.01); *A61M 2016/003* (2013.01); *A61M 2205/3327* (2013.01); *A61M 2205/84* (2013.01); *G01N 33/0009* (2013.01)
(58) Field of Classification Search
 CPC ................ A61M 16/022; A61M 16/16; A61M 2016/003; A61M 2016/0033; G01N 1/2247; G01N 33/0009; G01N 33/0018; G01N 33/004; G01N 33/0063; G01N 2001/2238; G01N 31/223; A62B 7/02
 See application file for complete search history.

(56) References Cited

U.S. PATENT DOCUMENTS

| | | | |
|---|---|---|---|
| 6,266,995 | B1 | 7/2001 | Scott |
| 7,014,691 | B2 * | 3/2006 | Lewin ................. B01D 53/261 55/315 |
| 2016/0287824 | A1 | 10/2016 | Chang |
| 2017/0014755 | A1 | 1/2017 | Harm et al. |

FOREIGN PATENT DOCUMENTS

| | | |
|---|---|---|
| DE | 603 01 390 T2 | 6/2006 |
| DE | 102010014222 A1 | 10/2011 |
| DE | 102012004249 A1 | 9/2013 |
| DE | 102012018697 B3 | 3/2014 |
| DE | 102010048518 B4 | 1/2021 |
| WO | 2017013472 A1 | 1/2017 |

* cited by examiner

US 11,530,965 B2

MONITORING DEVICE FOR A SYSTEM FOR GENERATING MEDICAL COMPRESSED AIR

CROSS REFERENCE TO RELATED APPLICATIONS

This application is a United States National Phase Application of International Application PCT/EP2018/063438, filed May 23, 2018, and claims the benefit of priority under 35 U.S.C. § 119 of German Application 10 2017 005 011.2, filed May 24, 2017, the entire contents of which are incorporated herein by reference.

TECHNICAL FIELD

The present invention pertains to a device for monitoring a system for generating medical compressed air. The compressed air is removed from the compressed air system downstream of a compressed air conditioning unit and is fed to the monitoring device via a measured air line. The monitoring device has at least one sensor, which generates a measured signal as a function of a property of the compressed air being fed through the measured air line. This measured signal is analyzed and information about the compressed air is made available to a user by means of an output unit.

TECHNICAL BACKGROUND

Compressed air generating systems are used in hospitals to supply medical compressed air through a network of compressed air supply lines to different compressed air consumers within the hospital. In this connection, the medical compressed air generated by the compressed air generating system is checked by a compressed air monitoring device for different parameters, and in particular for the concentration of relevant gases. Foreign gas concentrations of sulfur dioxide and nitrogen dioxide, for example, are detected in this manner to ensure that a medically flawless medical compressed air can be made available to the compressed air consumers.

For the necessary measurements, devices are used in the compressed air monitoring device to detect the relevant parameters of the medical compressed air. It should be taken into account that medical compressed air, as a drug, is subject to the European Pharmacopoeia, so that correspondingly high requirements, which are listed in DIN EN ISO 7396-1, are placed on the quality of this compressed air. According to this standard, predefined concentrations of carbon dioxide, carbon monoxide, oil, sulfur dioxide, nitrogen oxide may not be exceeded. Furthermore, oxygen must be present in the compressed air with a content of 20.4 vol. % to 21.4 vol. %. In order to be able to meet the above-described requirements on medical compressed air, this medical compressed air is purified by means of a treatment device with filters and dehumidified by a dehumidifier, wherein the moisture content is less than 67 ppm.

In addition to the permanent monitoring of the compressed air, it is, furthermore, necessary to take compressed air samples from the compressed air system at regular intervals, to analyze these air samples in order to be able to determine whether the compressed air monitoring system is operating flawlessly. Special taps, which make possible a corresponding removal of compressed air from the compressed air system, are usually provided for this.

A compressed air monitoring device, which permanently monitors the compressed air generated by means of a compressed air conditioning system with regard to its properties and taking into account the legal regulations, is known from DE 10 2010 014 222 A1. The compressed air monitoring device being described has as an essential component a humidifier that humidifies the compressed air fed to the sensors via a measuring line, so that drying out of the sensors is avoided in a reliable manner. The humidifier in this case preferably has a semipermeable, water-impermeable membrane which absorbs no harmful gases, for example, carbon monoxide, sulfur dioxide or nitrogen dioxide, and, moreover, also does not let any harmful gases diffuse through to the other side in case of an excess pressure on one side of the membrane.

SUMMARY

Based on the above-mentioned known state of the art, a basic object of the present invention is to perfect a device for monitoring a system for supplying consumers with medical compressed air in that monitoring of the generated medical compressed air within legal regulations is made possible with relatively low technical effort and thus in a relatively cost-effective manner. At the same time, taking compressed air samples shall be possible in a simple manner. Furthermore, by means of the compressed air monitoring device suggested, a compact arrangement of the sensors and components shall be accomplished, and an advantageous technical solution shall be provided for monitoring the concentration of carbon monoxide in the compressed air.

The present invention pertains to a compressed air monitoring device for a system for generating medical compressed air with a measured air line for removing compressed air from a compressed air supply line downstream of a compressed air conditioning unit. The compressed air monitoring device has at least one sensor for generating a measured signal as a function of a property of the compressed air fed through the measured air line, at least one humidifier for humidifying the compressed air upstream of the sensor and at least one output unit which outputs information about the property of the compressed air to a user on the basis of the measured signal. The present invention is characterized in that a tap is provided for removing compressed air and an actuator is provided for setting a volume flow and/or mass flow prevailing in the measured air line, wherein the actuator is inserted into the tap in a measuring mode and is removed from the tap in a compressed air removal mode. The essential technical feature of the present invention is thus based on the fact that a conventional tap, as it is also used for connection to compressed air consumers, is used for taking a compressed air sample, on the one hand, and an actuator (flowmeter) is inserted into the tap or into the compressed air port, on the other hand. It is thus possible in a relatively simple manner during the operation of the compressed air monitoring device to alternate between a measuring mode, in which a volume flow and/or mass flow measurement is carried out and a compressed air removal mode, in which a compressed air sample is taken from the compressed air system via the tap. It is, in principle, likewise conceivable to utilize the tap with its coupling for connection to a compressed air consumer, as soon as the actuator is not in the inserted state.

The actuator is preferably configured such that different discrete desired values can be set for the volume flow and/or mass flow prevailing in the measured air line. The actuator is preferably configured such that volume flow values of 0

L/min, 0.1 L/min, 0.2 L/min, 0.3 L/min, 0.4 L/min, 0.5 L/min, 0.6 L/min, 0.8 L/min or 1 L/min can be set in the measured air line. A configuration of the actuator, in which at least desired values are set for the volume flow of 0.1 L/min or 0.2 L/min, is especially advantageous.

According to a special embodiment, the actuator has at least one diaphragm, which brings about an adjustment of the volume flow. The actuator may be manual, for example, by providing a switch, which can be locked or actuated in an automated manner in different positions. It is generally conceivable that the actuator can be actuated by an external apparatus via a suitable interface and that data can be exchanged, as needed, unidirectionally or bidirectionally between the actuator and an external apparatus. It is otherwise advantageous if the actuator has a display unit, via which at least one operating parameter, especially the set desired value of the volume flow and/or mass flow prevailing in the measured air line, is outputted at least at times. As needed, the actuator has in a suitable manner its own supply unit with battery or storage battery for supplying with electrical energy or is to be supplied with electrical energy via an external power supply.

According to a special embodiment of the present invention, the tap is arranged downstream of the compressed air conditioning unit and upstream of the humidifier, which humidifies the compressed air before it is fed to the sensors. It is ensured in this manner that a compressed air sample can be taken, which has the parameters likewise present in the compressed air supply system.

The actuator can advantageously be inserted into the tap and removed from the tap in a manner free from destruction and without using tools for setting the volume flow and/or mass flow prevailing in the measured air line. In this connection, it shall be clearly expressed that it is advantageous if the corresponding actuator is inserted in a relatively simple manner into the tap, which is preferably configured as a conventional compressed air coupling, and can also be removed again.

According to a special variant of the present invention, the at least one sensor is configured as an electrochemical sensor to detect a property of the compressed air. Such a sensor is characterized in that it generates a measuring current as a function of the gas concentration of a specific gas in the measured compressed air, which measuring current is present as a measured signal and is analyzed with a suitable analyzer. The measured signal thus obtained is finally fed to an output unit, which outputs information about the measured property of the compressed air, especially the concentration of the specific gas, to a user. At least one sensor is especially advantageously provided, which detects the concentration of carbon monoxide (CO) within the medical compressed air generated. It is essential here that the CO concentration within the air be provided downstream of all compressed air conditioning units.

According to a special variant, a flowmeter is further provided, with which the volume flow and/or mass flow in the measuring gas line is measured and monitored. It is generally conceivable in this connection that the value measured by the flowmeter is used to monitor the setting of the actuator and to set to the needed value, as needed. Provisions are made in a very special embodiment of the presents invention for the value of the current volume flow, which value is determined by the flowmeter, to be used to adjust the actuator preferably in an automated manner, as least provided that the current value of the volume flow deviates from the desired value.

In a special embodiment of the present invention, exclusively the carbon monoxide concentration of the compressed air is monitored by means of a compressed air monitoring device configured according to the present invention. In this case, the compressed air monitoring device has a sensor for detecting the CO concentration in the compressed air, a humidifier for humidifying the air in the measured gas line and a tap with an actuator, which can be inserted into the tap or can be removed from same.

The above-mentioned components are preferably accommodated in a housing, so that a relatively compact unit is provided for monitoring the CO content of a compressed air flow, which at the same time makes it possible to be able to take a compressed air sample in a simple manner. A flowmeter is also preferably arranged in the housing to measure the volume flow of the compressed air within the measured air line.

The compressed air monitoring device configured according to the present invention advantageously has at least one dew point sensor. The humidity of the compressed air is monitored in this manner, and it is ensured that the above-described moisture content is not exceeded. It is, in principle, also conceivable in this connection to measure the humidity of the compressed air in the measured gas line in the flow direction behind the humidifier and/or behind the sensor for detecting a property of the compressed air in order to ensure that the respectively necessary humidity is present, but it is not too high.

According to a special embodiment of the present invention, the output unit is configured to display at least one concentration of a gas contained in the compressed air on a display unit or on a display. It is otherwise advantageous if the output unit is further configured to generate an alarm signal when exceeding or falling below a limit value for a property of the compressed air, especially the concentration of a specific gas. According to another special configuration of the output unit, a transmission unit is, furthermore, provided, so that a corresponding alarm can be transmitted to an external apparatus. Such a transmission can be carried out both in a wired manner and in a wireless manner. It is absolutely conceivable here that such an alarm is transmitted to a central monitoring device, for example, with an alarm server, or to locally arranged apparatuses that are carried along by the monitoring staff in charge.

In order to make possible an as compact as possible compressed air monitoring device, provisions are further advantageously made for the at least one sensor for detecting a property, especially a gas concentration, of the compressed air, the humidifier and the tap to be arranged in a housing. Such a housing is preferably a cabinet, especially a metal cabinet, which can be securely closed by means of a door. It is conceivable here that the necessary electronic components for controlling and for monitoring the compressed air monitoring device are likewise provided in such a housing. It is also conceivable that these components are arranged adjacent to the housing, in which the sensor for detecting a property of the compressed air, the humidifier and the tap are provided.

As an alternative or in addition to using electrochemical sensors for detecting a property of the compressed air, it is likewise possible to use infrared sensors, which are thus based on an optical measuring principle. The present invention is generally not limited to the use of a special type of sensor. Rather, sensors, which use different measuring principles, can each be used for use in the compressed air monitoring device according to the present invention, provided that they can detect a property of the compressed air, especially the concentration of a gas present in the compressed air, in a suitable manner.

With the system described, not only is the monitoring of the medical compressed air, especially in a compressed air supply system of a hospital, advantageously possible, but also, moreover, the alarm generation as well as complete documentation of the properties of the compressed air are possible.

In addition to a compressed air monitoring device, the present invention also pertains to a compressed air generation system, which is combined with a compressed air monitoring device configured according to the present invention. Such a compressed air generation system for a hospital comprises here an air compressor, which is configured, for example, as a reciprocating compressor or as a screw-type compressor for compressing ambient air to form medical compressed air, a dehumidifier for dehumidifying the ambient air taken in and the compressed air monitoring device configured according to the present invention for monitoring at least one parameter of the medical compressed air.

All alarms generated by the compressed air monitoring device are preferably transmitted to an alarm management system, which makes possible both a central and a local alarm generation. The recorded measured parameters and/or the respectively generated alarms are preferably documented continually, so that not only is a provision of medical compressed air ensured at any time, but also, moreover, aberrations within the compressed air generation system or compressed air provision system are detected at an early stage.

The present invention will be explained in more detail below without limiting the general idea of the present invention on the basis of exemplary embodiments and with reference to the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
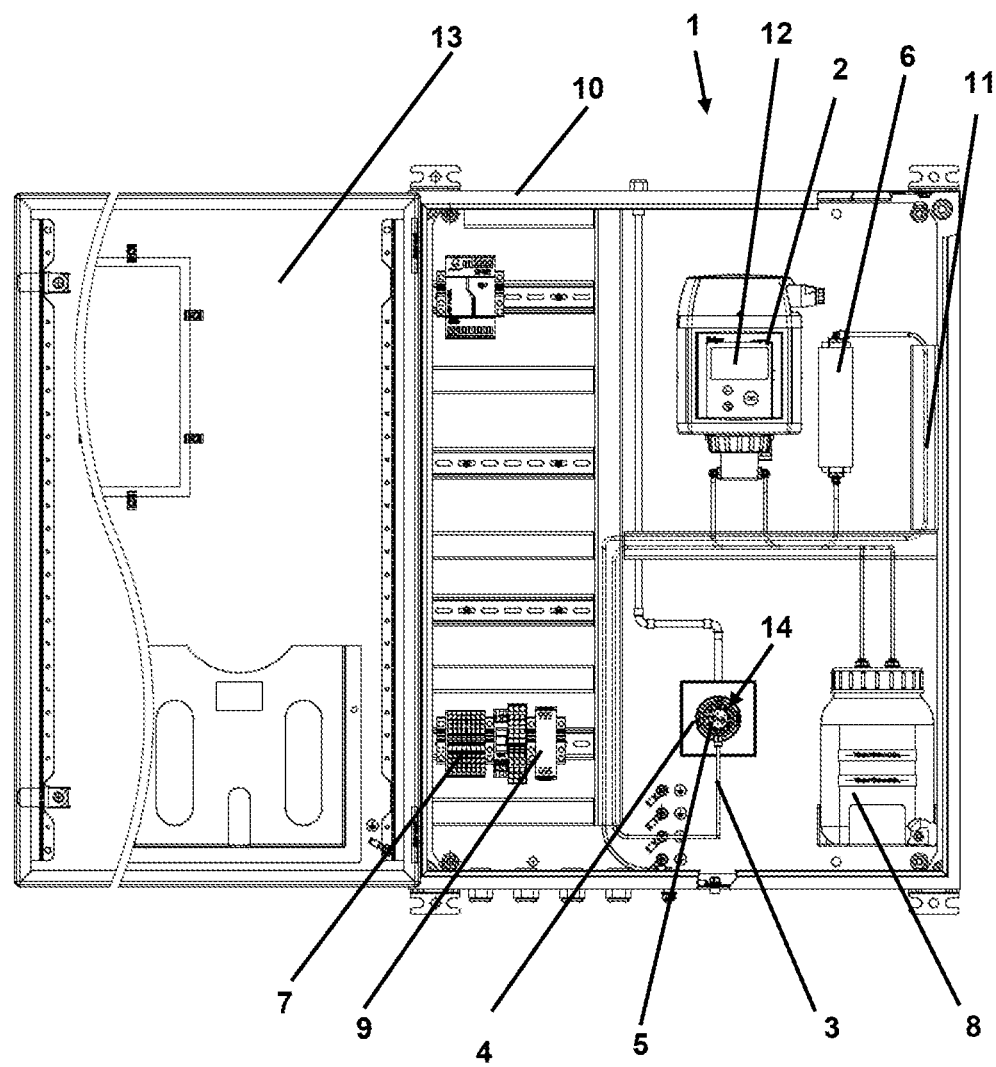
FIG. 1 is a side view showing a compressed air monitoring device with integrated tap, into which an actuator for setting the volume flow is inserted.

Referring to the drawings, FIG. 1 shows a compressed air monitoring device 1 configured according to the present invention, with which medical compressed air provided by a compressed air conditioning unit is monitored. The compressed air monitoring device 1 has for this purpose a sensor 2 for detecting a property of the compressed air, which is configured as an electrochemical sensor 2 according to this exemplary embodiment. The electrochemical sensor 2 can determine the concentration of carbon monoxide (CO) in the compressed air generated by the compressed air conditioning unit. The compressed air monitoring device 1 being shown is arranged downstream of the compressed air conditioning unit, which has essentially a compressor and a dehumidifier. No other technical devices are arranged between the compressed air conditioning unit and the compressed air monitoring device 1 shown in FIG. 1.

The compressed air monitoring device 1 essentially has a measured air line 3, via which compressed air is removed from the compressed air supply system and is finally fed to the electrochemical sensor 2 for detecting the carbon monoxide concentration in the compressed air.

The medical compressed air admitted into the compressed air supply lines from the compressed air generation system is reduced via a pressure reducer to a pressure of, for example, 1.2 bar with a volume flow of no more than about 1.0 L/min and is fed into the measured air line 3. The volume flow within the measured air line 3 is first set to a value of 0.1 L/min or 0.2 L/min by means of the actuator 5 inserted into a tap 4, which is configured as a compressed air coupling 14. The volume flow prevailing in the measured air line is monitored by means of the flowmeter 6. Provided that the setting of the volume flow is carried out in an automated manner, this takes place taking into account a desired volume flow value stored in the control unit 7 as well as the actual value of the volume flow, which actual value of the volume flow is measured by the flowmeter 6.

The CO sensor 2, with which the concentration of carbon dioxide in the compressed air is detected, is an essential component of the compressed air monitoring device 1. In order to not permanently damage the CO sensor 2 due to the supplied compressed air having been dried, a humidifier 8 is arranged upstream of the CO sensor 2, with respect to the flow direction. The humidifier 8 has a fluidtight housing. A flexible tube made of a semipermeable, water-impermeable membrane, for example, made of Nafion polymer (sulfonated tetrafluoroethylene based fluoropolymer-copolymer), is arranged within the housing of the humidifier 8. The flexible tube also forms the measured air line 3 within the housing of the humidifier 8.

The medical compressed air is fed through the flexible tube through a space enclosed by the housing of the humidifier 8.

A saturated water-salt solution is located within the space enclosed by the housing of the humidifier 8, wherein the salt, preferably magnesium chloride, is located on a bottom of the space enclosed by the housing of the humidifier 8. Moist air with a constant relative humidity in the range of approximately 30% is located above the water-salt solution.

According to the exemplary embodiment explained here, medical compressed air with a volume flow of 0.1 L/min or 0.2 L/min is fed through the measured air line 3 and thus through the flexible tube in the interior of the humidifier 8. The flexible tube is dimensioned such that it has a sufficient length and surface, so that the moisture of the moist air is diffused through the flexible tube into the medical compressed air and this compressed air is moistened to a relative humidity in the range between 25% and 30%.

After the moistening of the medical compressed air, this moistened medical compressed air is forwarded via the measured air line 3 and at first is guided through the flowmeter 6 before it is sent to the CO sensor 2. In this manner, the sensor receives medical compressed air with a constant relative humidity in the range between 25% and 30%, so that the CO sensor 2 cannot dry out and can be used reliably over a longer time, which is preferably longer than six months. A frequent replacement of the CO sensor 2 can thus be reliably avoided.

The actuator 5 is provided for setting the volume flow to be able to set the volume flow within the measured gas line 3 to a desired value. This actuator 5 has a port, which is configured such that the actuator 5 can be inserted into a conventional compressed air coupling 14 for compressed air consumers. A tool is neither necessary for an insertion of the actuator 5 into the conventional compressed air coupling 14 nor is a tool necessary for a removal of the actuator 5 out the conventional compressed air coupling 14 of the tap 4. In the exemplary embodiment shown in FIG. 1, the actuator 5 is located in the inserted position in the tap 4, which is configured as a compressed air coupling 14.

As long as the actuator 5 for setting the volume flow is inserted into the tap 4, a constant volume flow is set within the measured air line 3 by the actuator 5. Different discrete volume flow values of 0.1 L/min, 0.2 L/min, 0.3 L/min, 0.4 L/min, 0.5 L/min, 0.6 L/min, 0.8 L/min, or 1.0 L/min can be set with the actuator 5, which has a diaphragm (diaphragm valve). A volume flow of 0.1 L/min or 0.2 L/min is preferably set at the actuator 5. The respectively set desired value for the volume flow is monitored by means of the flowmeter 6. A manual or automated adjustment of the actuator 5 can advantageously be carried out based on the values for the current volume flow, which values are determined with the flowmeter 6. Furthermore, corresponding measured values may be transmitted to a central analyzer 9 by wire (in a wired manner or preferably wirelessly (in a wireless manner). Moreover, the measured signals generated by a suitably configured flowmeter 6 can be used to set the volume flow flowing through the measured air line 3 to the CO sensor 2 by means of the actuator 5. The actuator 5 can be automatically adjusted (in an automated manner) with the measured signals generated by the flowmeter 6 based on the actuator having the diaphragm valve or another control valve.

The compressed air monitoring device 1 shown in FIG. 1 for the permanent monitoring of the CO content of medical compressed air is arranged in a compact manner within a housing 10. The CO sensor 2, the tap 4 with the actuator 5 inserted in it, the humidifier 8 and the flowmeter 6 are thus arranged in the housing 10, which can be closed by a door 13. Furthermore, an illuminating unit 11 is provided in order to carry out work even under poor light conditions at the compressed air monitoring device 1, especially to read measured values for the CO concentration from an output unit 12 or to take a compressed air sample via the tap 4.

The volume flow within the measured air line can advantageously be set by means of this actuator 5. If the flowmeter 6 is coupled to the actuator 5 in a controlled manner, the volume flow in the measured air line 3 can be changed as a function of the measured signal generated by the flowmeter 6. The degree of automation of the compressed air monitoring device 1 and also the manner of data transmission can generally be adapted to the conditions in the respective hospital. The CO sensor 2 may have different data interfaces as a function of these conditions or the present requirements. As a function of need, either an analog measured signal of 4-20 mA can be generated or the signal transmission takes place via a BUS system, for example, HART, LON, Profibus or Foundation-Fieldbus.

Figure 2:
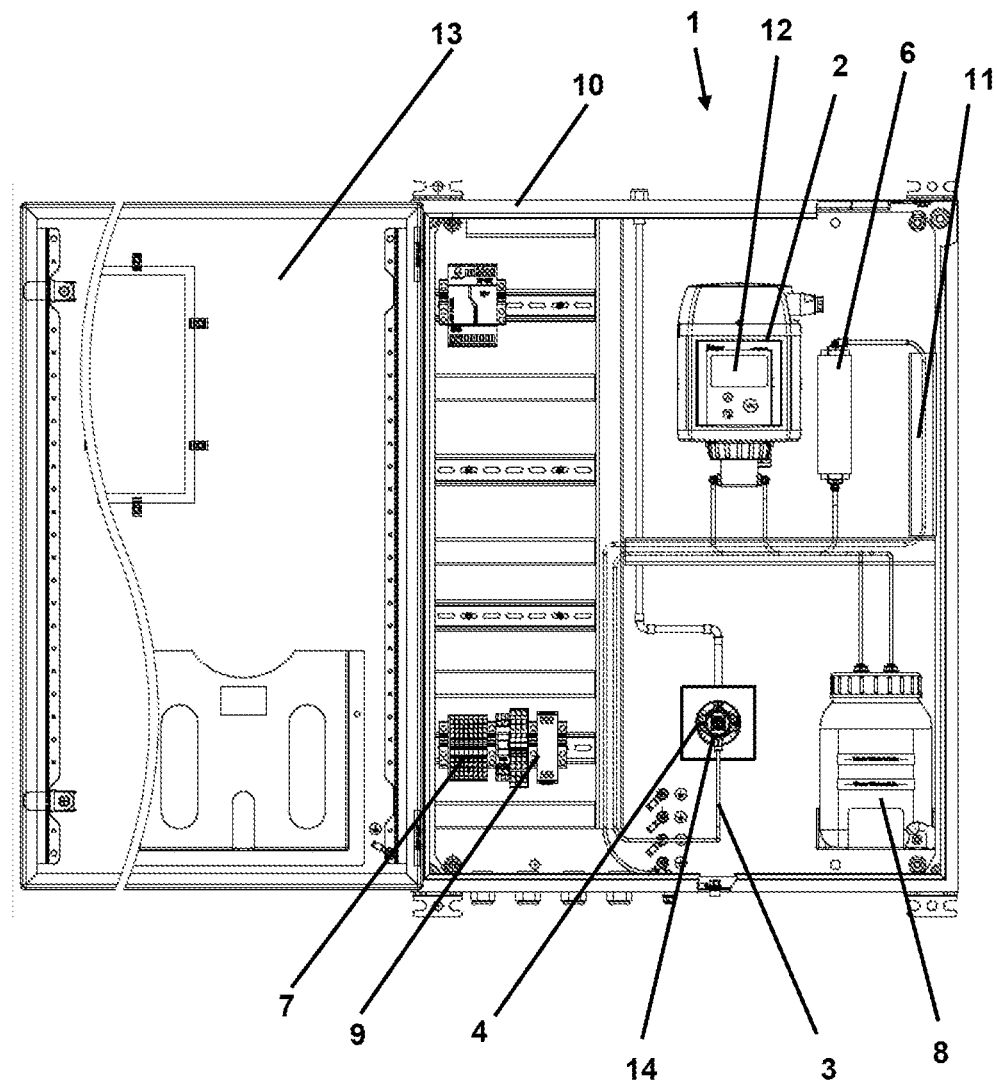
FIG. 2 is a side view showing a compressed air monitoring device with integrated tap, into which no actuator for setting the volume flow is inserted.

FIG. 2 shows a compressed air monitoring device 1 configured according to the present invention, which has the same components as they were already explained in connection with FIG. 1. Identical components are identified by the same reference numbers. It is essential that just as in FIG. 1, all components are arranged compactly in a closable housing 10. By contrast to the operating state, as it is shown in FIG. 1, the actuator 5 in the view according to FIG. 2 is not located within the tap 4, which is configured as a compressed air coupling 14. Rather, the compressed air coupling 14 is freely accessible in this operating state in the compressed air removal mode and can be used as a tap 4 for taking a compressed air sample from the compressed air system. As soon as the regularly carried out compressed air removal is completed, the actuator 5 can in turn be inserted into the compressed air coupling, so that a constant volume flow again permanently flows through the measured air line 3 corresponding to the setting of the actuator 5.

The technical solution according to the present invention thus makes it possible to combine the measurement of a carbon monoxide concentration in medical compressed air with the possibility of taking individual compressed air samples in a relatively simple manner.

While specific embodiments of the invention have been shown and described in detail to illustrate the application of the principles of the invention, it will be understood that the invention may be embodied otherwise without departing from such principles.

The invention claimed is:

1. A monitoring device for monitoring a system for generating medical compressed air, the monitoring device comprising:
   a measured air line for removing compressed air from a compressed air supply line downstream of a compressed air conditioning unit;
   a sensor for generating a measured signal as a function of a property of the compressed air fed through the measured air line;
   a humidifier for humidifying the compressed air upstream of the sensor;
   an output unit for outputting information about the property of the compressed air to a user on the basis of the measured signal;
   a tap for removing compressed air; and
   an actuator for changing a volume flow and/or mass flow of the compressed air, which volume flow and/or mass flow prevails in the measured air line, wherein the actuator is inserted into the tap in a measuring mode and is removed from the tap in a compressed air removal mode.

2. A monitoring device in accordance with claim 1, wherein the actuator is configured to set different discrete values of the volume flow and/or mass flow in the measured air line.

3. A monitoring device in accordance with claim 1, wherein the actuator is configured to set at least volume flows of $1.67 \times 10^{-6}$ m$^3$/sec (0.1 L/min) or $3.33 \times 10^{-6}$ m$^3$/sec (0.2 L/min).

4. A monitoring device in accordance with claim 1, wherein the actuator has at least one diaphragm valve.

5. A monitoring device in accordance with claim 1, wherein:
   the actuator is insertable into the tap and removeable from the tap without destruction thereof for setting the volume flow and/or mass flow prevailing in the measured air line; or
   the actuator is insertable into the tap and removeable from the tap without using tools for setting the volume flow and/or mass flow prevailing in the measured air line; or
   the actuator is insertable into the tap and removeable from the tap without destruction thereof and without using tools for setting the volume flow and/or mass flow prevailing in the measured air line.

6. A monitoring device in accordance with claim 1, wherein the sensor is configured as an electrochemical sensor for detecting at least one property of the compressed air.

7. A monitoring device in accordance with claim 1, wherein the sensor is configured as a CO sensor for detecting at least one property of the compressed air, which CO sensor generates the measured signal as a function of the CO content of the compressed air.

8. A monitoring device in accordance with claim 1, wherein the output unit is configured to display at least one concentration of a gas in the compressed air on the output unit.

9. A monitoring device in accordance with claim 1, wherein the output unit is configured to generate an alarm signal when exceeding or falling below a limit value for the property of the compressed air.

10. A monitoring device in accordance with claim 1, wherein the output unit has a transmission unit, via which the information about the property of the compressed air can be transmitted to an external apparatus.

11. A monitoring device in accordance with claim 1, further comprising a housing, wherein the sensor for detecting at least one property of the compressed air, the humidifier and the tap are arranged in the housing.

12. A monitoring device in accordance with claim 11, further comprising at least one illuminating unit arranged in the housing.

13. A monitoring device in accordance with claim 11, further comprising a control unit and/or an analyzer are arranged in the housing.

14. A monitoring device in accordance with claim 1, wherein a sensor for detecting the carbon monoxide concentration is provided exclusively as the sensor for detecting a property of the compressed air.

15. A monitoring device in accordance with claim 1, further comprising a flowmeter for measuring the volume flow and/or mass flow prevailing in the measured air line.

16. A system for generating and distributing medical compressed air, the system comprising:
    a compressed air supply line downstream of a compressed air conditioning unit; and
    a monitoring device, the monitoring device comprising:
    a measured air line for removing compressed air from the compressed air supply line downstream of the compressed air conditioning unit;
    a sensor for generating a measured signal as a function of a property of the compressed air fed through the measured air line;
    a humidifier for humidifying the compressed air upstream of the sensor;
    an output unit for outputting information about the property of the compressed air to a user on the basis of the measured signal;
    a tap for removing compressed air; and
    an actuator for changing a volume flow and/or mass flow of the compressed air, which volume flow and/or mass flow prevails in the measured air line, wherein the actuator is inserted into the tap in a measuring mode and is removed from the tap in a compressed air removal mode.

17. A system in accordance with claim 16, wherein the actuator is configured to set different discrete values of the volume flow and/or mass flow in the measured air line.

18. A system in accordance with claim 17, wherein the actuator comprises a diaphragm valve.

19. A system in accordance with claim 17, wherein:
    the actuator is insertable into the tap and removeable from the tap without destruction thereof for setting the volume flow and/or mass flow prevailing in the measured air line; or
    the actuator is insertable into the tap and removeable from the tap without using tools for setting the volume flow and/or mass flow prevailing in the measured air line; or
    the actuator is insertable into the tap and removeable from the tap without destruction thereof and without using tools for setting the volume flow and/or mass flow prevailing in the measured air line.

20. A system in accordance with claim 17, wherein:
    the sensor is configured as an electrochemical CO sensor configured to generate the measured signal as a function of the CO content of the compressed air;
    the output unit is configured to display a CO concentration in the compressed air on the output unit;
    the output unit is configured to generate an alarm signal when exceeding or falling below a limit value for the the CO concentration of the compressed air;
    the output unit has a transmission unit, via which the information about the property of the compressed air can be transmitted to an external apparatus.

* * * * *